United States Patent [19]

Buriks et al.

[11] 4,310,472

[45] Jan. 12, 1982

[54] QUATERNARY AMMONIUM ADDUCTS OF POLYMERIZABLE TERTIARY AMMONIUM SALTS AND ACRYLONITRILE

[75] Inventors: Rudolf S. Buriks; Allen R. Fauke; David W. Griffiths, all of St. Louis, Mo.

[73] Assignee: Petrolite Corporation, St. Louis, Mo.

[21] Appl. No.: 133,047

[22] Filed: Mar. 24, 1980

Related U.S. Application Data

[62] Division of Ser. No. 955,443, Oct. 27, 1978, Pat. No. 4,230,839, which is a division of Ser. No. 523,813, Nov. 14, 1974, Pat. No. 4,179,549.

[51] Int. Cl.$^3$ ............................................. C07C 121/16
[52] U.S. Cl. .................................. 260/465.4; 560/222; 564/159; 564/197
[58] Field of Search .......... 260/561 K, 561 A, 561 N, 260/465.4; 560/222; 564/159, 197

[56] References Cited

U.S. PATENT DOCUMENTS

| | | | |
|---|---|---|---|
| 3,170,901 | 2/1965 | Melamed et al. | 560/222 |
| 3,336,358 | 8/1967 | McFadden | 560/222 |
| 3,962,332 | 6/1976 | Trapaso | 260/56 W |
| 4,009,201 | 2/1977 | Steckler et al. | 560/222 |
| 4,180,643 | 12/1979 | Moss et al. | 260/56 W |

OTHER PUBLICATIONS

Erickson, J. Am. Chem. Soc., 74, (1952), pp. 6281-6282.

*Primary Examiner*—Arthur P. Demers
*Attorney, Agent, or Firm*—Sidney B. Ring; Hyman F. Glass

[57] ABSTRACT

This invention relates to adducts of salts of polymerizable tertiary amines with acrylic compounds illustrated by acrylamide and acrylonitrile; to polymers and copolymers containing said adducts and to processes for preparing them. This invention also relates to the use of said polymers and copolymers, particularly in the clarification of turbid waters by flocculation or flotation of oil and/or suspended solids. In the preferred embodiment, the quaternary adduct monomer is:

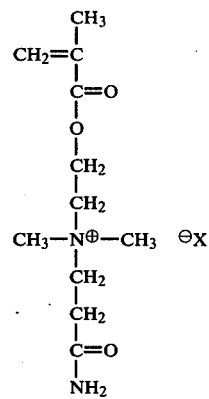

where X is an anion, preferably halide such as chloride or carboxylate such as acetate; and polymers and copolymers containing units thereof.

5 Claims, No Drawings

QUATERNARY AMMONIUM ADDUCTS OF POLYMERIZABLE TERTIARY AMMONIUM SALTS AND ACRYLONITRILE

This is a division, of application Ser. No. 955,443, filed October 27, 1978, now U.S. Pat. No. 4,230,839, which is a division of application Ser. No. 523,813, filed Nov. 14, 1974, now U.S. Pat. No. 4,179,549, issued on Dec. 18, 1979.

This invention relates to adducts of salts of polymerizable tertiary amines with acrylic compounds illustrated by acrylamide and acrylonitrile; to polymers and copolymers containing said adducts and to processes for preparing them. This invention also relates to the use of said polymers and copolymers, particularly in the clarification of turbid waters by flocculation or flotation of oil and/or suspended solids.

When a mixture of two acrylic monomers is polymerized, a copolymer containing the respective monomer units is formed. Thus a mixture of acrylamide and acrylic acid will yield a random copolymer which can be represented as follows:

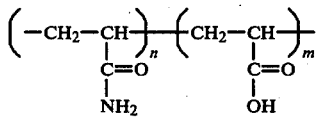

When acrylamide (AM) is copolymerized with the acetate salt of dimethylaminoethyl methacrylate (DMAEMA-acetate) one expects the following copolymer to form:

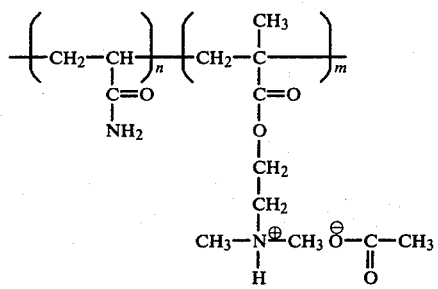

We have now discovered that actual formation of this copolymer requires specific reaction conditions and that generally when acrylamide is copolymerized with DMAEMA acetate the following terpolymer is formed:

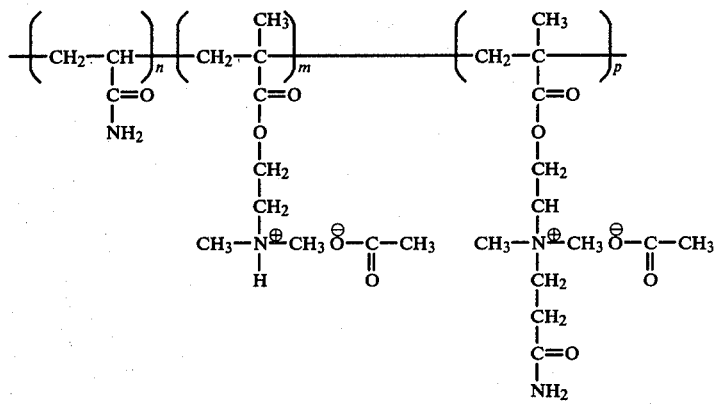

We have now discovered that this terpolymer is formed due to the generation of quaternary ammonium adduct groups from tertiary ammonium salt groups and acrylamide:

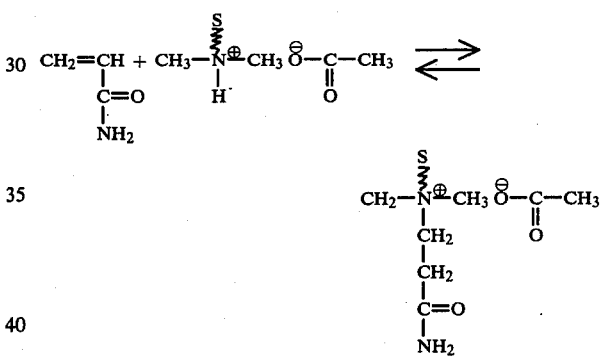

where S represents either the monomer or copolymer residue. This adduct formation can take place before, during and after the copolymerization reaction.

The present invention relates to adducts formed before or during the copolymerization reaction.

The adducts described herein are quaternary ammonium salts, variously referred to as such, as adducts, as quaternary adducts, as quaternary ammonium adducts, or simply as quats.

The principal method of the present invention involves reaction of a conjugate acid salt of a tertiary amine with acrylamide according to the following equation

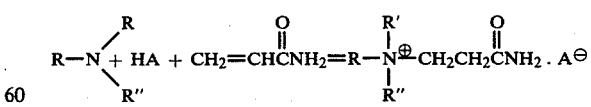

HA = an acid whose anion is A.

Two of the R, R', and R'' groups are substituted groups, preferably alkyl and most preferably methyl groups to minimize steric hindrance around the nitrogen atom and thus maximize reaction rate. The third group may be an hydroxyethyl or a methacryloxy-ethyl group. The acid used to form the conjugate acid of the tertiary amine may be an aliphatic carboxylic acid such as acetic acid or a mineral acid such as hydrochloric acid.

Reaction of the tertiary ammonium salt with acrylamide may be conducted in either an aqueous or nonaqueous solvent. Nonaqueous solvents are advantageous for isolation of the quaternary ammonium salt. In 2-propanol, for example, crystallization of the quaternary ammonium salt shifts the equilibrium in the desired direction. The crystallized product, in most cases, requires no further purification.

Reactions in nonaqueous solvents are preferably conducted with half-neutralized amines at temperatures of 0°–25°. To maximize reaction rate, total reactant concentration should be as high as possible without exceeding the solubility of the least soluble component. The ratio of total amine molar concentration to acrylamide concentration is preferably between 1/10 and 4/1.

For most purposes, isolation of the quaternary ammonium salt is unnecessary and in these cases, the reaction is preferably conducted in aqueous solution at a temperature of from 0° to 100° at atmospheric pressure and at a pH of from 5 to 9. Reaction rate increases with increasing temperature and with increasing pH. The equilibrium constant for formation of the quaternary ammonium salt, however, decreases with increasing temperature and is independent of pH within the specified range. Preferred temperature and pH range for formation of the quaternary ammonium salt are 25°–50° and pH 6–8, respectively.

At fixed temperature and pH, the equilibrium concentration of quaternary ammonium salt may be increased by increasing the total reactant concentration and/or by increasing the acrylamide to amine concentration ratio. For example, at an initial total amine concentration of 1 mole/liter and 1/1 molar ratio of acrylamide to amine, less than 50% of the amine is converted to a quaternary ammonium salt at 55° and pH-7.0. But, at the same temperature and pH, equilibrium conversion in excess of 90% can be achieved by employing an initial amine concentration of 3 mole/liter and a 3/1 molar ratio of acrylamide to amine. At any reactant concentration and at any ratio of acrylamide to amine, quaternary ammonium content at equilibrium is governed by the relationship, $$Qe = \frac{K(n+1)R_3N_0 + 1 - [K^2(n-1)^2R_3N_0^2 + 2K(n+1)R_3N_0 + 1]^{\frac{1}{2}}}{2K}$$

where $Qe$ = the equilibrium concentration of quaternary ammonium salt, $R_3N_0$ = the initial concentration of tertiary amine, $n$ = the ratio of initial acrylamide concentration to initial amine concentration, and $K$ = the equilibrium constant for formation of the quaternary ammonium salt. Values of K for conversion of N,N-dimethyl-N-(2-hydroxyethyl) ammonium chloride to its quaternary ammonium chloride, useful for approximating extent of conversion of similar tertiary amines to their quaternary ammonium salts, are found to be 3.2 M$^{-1}$ at 25°, 2.0 M$^{-1}$ at 55°, and 0.7 M$^{-1}$ at 85°. These equilibrium constants are invariant over a pH range of 5.8 to 7.8.

In the case of hydrolyzable amines such as acrylic or methacrylic acid esters of alkanolamines, care must be exercised to minimize the extent of hydrolysis during the quaternization reaction. Rates of hydrolysis, like rates of quaternization, are increased by increasing temperature as well as by increasing pH. Rates of quaternization may be maximized with respect to rates of hydrolysis, however, by applying the principles outlined above; i.e., by employing high reactant concentrations and high ratios of acrylamide to amine. Thus, for hydrolyzable amines, total reactant concentrations of about 30–50% by weight and molar ratios of acrylamide to amine in excess of about 2/1 are preferred.

In the case of polymerizable amines, the amine may be converted with acrylamide to its quaternary ammonium salt prior to polymerization. The isolated material undergoes homopolymerization or copolymerization with acrylamide when excess acrylamide is added to the monomer mixture. Alternatively, the quaternary ammonium salt of a polymerizable tertiary amine may be prepared in situ. A free radical initiator may be added to the reaction mixture at the beginning of the quaternization reaction or after a time interval sufficient to ensure equilibration prior to polymerization. In either case, the quaternary ammonium salt undergoes vinyl copolymerization with its constituent parts, with excess acrylamide, and with hydrolysis products, if present, to form cationic polyelectrolytes. By applying the principles outlined above, copolymers containing from <1 to >99% quaternary ammonium groups (based on total amine) can be prepared. For example, polymerization of a mixture of acrylamide (2 equivalents) and dimethylaminoethyl methacrylate (1 equivalent) at a concentration of 50% by weight in an aqueous solution (pH=7.0) at 85° produces a copolymer with <5% quaternary ammonium salt content. However, polymerization of the same monomer mixture at 55° produces a copolymer with 50–60% quaternary ammonium salt content provided that reaction is discontinued after about 6 hrs.

The methods described herein are applicable as well to the preparation of polymeric quaternary ammonium salts from polymeric tertiary amines. For example, homopolymers of dimethylaminoethyl methacrylate are converted, in part, to polyquats by treatment with acrylamide in aqueous solution at pH-7.8 and 60°. Since polymers of hydrolyzable tertiary amine monomers are more stable toward hydrolysis than the respective monomers, elevated temperatures (60°–100°) and elevated pH values (7–9) may be employed and, in fact, are preferred for quaternization of preformed polymers.

The polymers described herein may be prepared by any method, such as by solution or emulsion polymerization. The polymeric products described herein are widely useful as flocculants and flotation aids. The method described herein for producing these materials is particularly advantageous in that the quaternary ammonium salt content can be deliberately varied to meet the demands of diverse uses.

The monomeric compositions of the invention are of the formula:

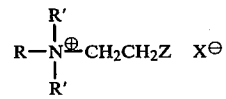

where R is a polymerizable group, the R's are substituted groups, Z is

or —CN, and X is an anion. R may be an alkylmethacryloxy or -methacrylamide group or alkyl-acryloxy, R' may be alkyl, Z may be

and X a chloride or a carboxyl moiety. Typically R is

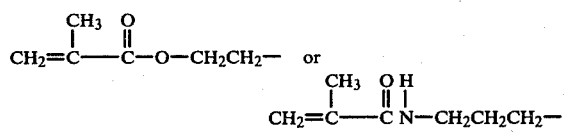

The polymers contain units of such monomeric compositions.

To assist those skilled in the art to practice this invention, the following examples are given. Concentrations are expressed in moles/liter (M) or in percent by weight. Temperature is expressed °C. Abbreviations of chemical compounds are as follows: AM=acrylamide; DMAE=N,N-dimethylethanolamine; DMAEMA=N,N-dimethylaminoethyl methacrylate; AN=acrylonitrile.

EXAMPLES

(1) Preparation of the DMAE-AM quaternary ammonium chloride 36 parts of AM, 89 parts of DMAE, and 126 parts of DMAE.HCl (1:1:2 molar ratio of AM:DMAE:DMAE.HCl) are dissolved in 500 parts of warm (40°–50°) 2-propanol. The solution is immediately cooled to 25° whereupon crystallization of the product begins within 10 min. After 16 hrs., the crystals are collected by filtration and dried in vacuo to give 98 parts (100% yield) of directly pure DMAE-AM quaternary ammonium chloride having mp=157°–158°.

(2) Preparation of the DMAE-AN quaternary ammonium chloride

As in example (1), 16 parts of AN, 55 parts of DMAE, and 78 parts of DMAE.HCl are dissolved in 450 parts of warm (40°–50°) 2-propanol. The solution is cooled to 25° then, after 48 hrs., filtered to give 32 parts (57%) of directly pure DMAE-AN quaternary ammonium chloride, mp=110°.

(3) Preparation of the DMAEMA-AM quaternary ammonium chloride 71 parts of AM, 79 parts of DMAEMA, 97 parts of DMAEMA.HCl, and 2 parts of phenothiazine are dissolved in 130 parts of 2-propanol by warming to 40°. The solution is cooled to 0° then, after 1 week, filtered to give 36 parts of DMAEMA-AM quaternary ammonium chloride as a crystalline solid. Concentration of the mother liquor to 50% of its initial weight, followed by cooling to 0° yields an additional 30 parts of quaternary ammonium chloride, raising the total isolated yield to 50%.

(4) Equilibration of the DMAE-AM quaternary ammonium chloride with its constituent parts A sample of a 2.54 M solution of the DMAE-AM quaternary ammonium chloride (prepared as described in example 1) in a pH-7.8 phosphate buffer is placed in an nmr sample tube. An nmr (nuclear magnetic resonance) spectrum is recorded within 10 min. of sample preparation. The nmr sample tube is then immersed in a constant temperature bath thermostatted at 55° and removed periodically for further nmr analysis. An equilibrium is approached, the singlet resonance of the N-methyl groups of DMAE.HCl ($\delta 2.95$) increases in area at the expense of the singlet resonance of the N-methyl groups of DMAE-AM quaternary ammonium chloride ($\delta 3.23$). Equilibrium is achieved within 6 hrs. at 55° (no further changes in the nmr spectrum occur thereafter) to produce a mixture containing 64.8% DMAE-AM quaternary ammonium chloride and 35.2% DMAE.HCl. Thus, the equilibrium concentrations of DMAE.HCl, and AM are 1.64 M, 0.90 M, and 0.90 M, respectively, and the equilibrium constant for formation of the quaternary ammonium salt, K, is 2.0 $M^{-1}$.

In like manner, the equilibrium constant for conversion of mixtures of DMAE.HCl and AM to DMAE-AM quaternary ammonium chloride has been evaluated as a function of total amine concentration at each of 3 pH values. The results are summarized in Table I.

TABLE I

| pH(25°) | Total Amine Concentration, M | Time Required for Equilibration, hr. | % Total Amine Quaternized at Equilibrium | K,$M^{-1}$ (55°) | Average K,$M^{-1}$ (55°) |
|---|---|---|---|---|---|
| 5.8 | 2.54 | 168 | 62.8 | 1.80 | |
| 5.8 | 1.52 | 168 | 55.9 | 1.89 | 1.8 ± 0.1 |
| 5.8 | 0.51 | 168 | 37.2 | 1.85 | |
| 7.0 | 2.54 | 24 | 64.7 | 2.02 | |
| 7.0 | 1.27 | 24 | 51.2 | 1.71 | 1.7 ± 0.2 |
| 7.0 | 0.76 | 24 | 41.9 | 1.60 | |
| 7.0 | 0.25 | 24 | 24.2 | 1.67 | |
| 7.8 | 2.54 | 6 | 64.8 | 2.02 | |
| 7.8 | 1.52 | 6 | 55.7 | 1.89 | 1.9 ± 0.1 |
| 7.8 | 0.51 | 6 | 37.7 | 1.92 | |

(5) Temperature dependence of the equilibrium constant for formation of the DMAE-AM quaternary ammonium chloride The equilibrium constant for formation of DMAE-AM quaternary ammonium chloride from mixtures of DMAE.HCl and AM has been evaluated at 85° and at 25° by the method described in example 4. All measurements were conducted in a phosphate buffer having pH=7.8. At 85°, equilibrium (approached from the quaternary ammonium salt) is achieved within 2 hrs. and is governed by the relationship: K=0.7 $M^{-1}$. At 25°, equilibrium requires 1 week and equilibrium is governed by the relationship: K=3.2 $M^{-1}$.

(6) Solution polymerization of DMAEMA-AM quaternary ammonium chloride 25 parts of DMAEMA-AM quaternary ammonium chloride (prepared as described in example 3) is dissolved in 225 parts of deionized water at 25°. The solution, having pH=6.0, is treated with 0.5 parts of 4,4'-azobis (4-cyanovaleric acid), degassed, then warmed to 50° under nitrogen whereupon polymerization occurs as indicated by a gradual increase in viscosity. After 30 min., an additional 0.5 parts of initiator is added and temperature is maintained at 50° for 1 hr. thereafter. Nmr analysis of the product solution shows >90% conversion of monomer to polymer and >95% retention of quaternary ammonium groups in the polymeric product.

(7) Reactions of poly(DMAEMA-AM quaternary ammonium chloride)

Aqueous solutions of poly(DMAEMA-AM quaternary ammonium chloride) buffered at pH=7.8 and at pH=5.8 are prepared by mixing equal parts of the polymer solution of example (6) and the appropriate phosphate buffer. Upon incubation at 58°, the buffered solutions are observed to undergo the changes summarized in Table II. The changes are not governed by an equilibrium relationship since AM produced by retroquaternization of the polymer is consumed by polymerization.

TABLE II

| | % Quaternary Ammonium Salt Remaining | |
|---|---|---|
| Time at 58° | pH = 7.8 | pH = 5.8 |
| 0 | >95 | >95 |
| 1 hr. | 69 | — |
| 3.5 hrs. | 47 | — |
| 5.5 hrs. | 38 | — |
| 1 day | <5 | 74 |
| 3 days | <5 | 54 |

(8) Reaction of polyDMAEMA with AM 200 parts of DMAEMA and 76.4 parts of acetic acid are dissolved in 1723 parts of deionized water to give a solution with pH=6.5. After initiating with 2 parts of 4,4'-azobis(4-cyanovaleric acid), polymerization is conducted at 60°, under nitrogen, for 1 hr. Residual monomer is removed by dialysis, and polymer is then isolated by lyophilization.

121 parts of the lyophilized polymer, 38 parts of AM, and 1 part of phenothiazine are then dissolved in 284 parts of a pH=7.8 phosphate buffer. Upon incubation at 58°, 10% of the tertiary amine groups are converted to quaternary ammonium groups within 6 hr.

(9) Emulsion polymerization of DMAEMA-acetate/acrylamide mixtures

General Method

The internal phase is an aqueous solution of the monomers. The external phase is a paraffin oil such as Shellflex 131, Ashland Mineral Seal Oil, or Isopar M. Both the emulsifier and the initiator are oil soluble. The advantage of this method is that a 30% active product will flow readily and has a viscosity in the range of 2000 to 2500 cps. An aqueous solution of these high molecular weight polymers would be gelled above 2% active concentration.

Prior to application the emulsion is inverted and dissolved in water to give a dilute solution. One part of a nonionic surfactant of the oxyethylated alkyl phenol type, such as Triton X-100 or Tergitol NP-33 is dissolved in 979 parts of water. Then 20 parts of the inverse emulsion polymer is added. After the mixture has been stirred for 30 minutes, the polymer has dissolved in water. The resulting solution is 0.6% active and has a viscosity in the range of 2600 cps. (Brookfield RVT at 5 rpm with #2 spindle.)

The principles of this invention are applied in the following examples to produce cationic polyelectrolytes of variable quaternary ammonium salt content. Within each set of examples, only one physical parameter is changed—all other variables are held constant. Thus, in examples 9A and 9B, quat content is varied by changing the AM to DMAEMA concentration ratio (an example of combined kinetic and thermodynamic control). In examples 9C through 9E, quat content is varied by changing the pH of the reaction medium (an example of kinetic control alone). In examples 9C and 9F, quat content is varied by changing the temperature of the reaction medium (an example of thermodynamic control alone).

EXAMPLE 9A

Acrylamide/DMAEMA 1/1 Molar

To a solution of 50 g of acetic acid in 410 grams of tap water is added 131 grams of DMAEMA followed by 59.5 grams of acrylamide. The pH is 7.0 without adjustment. This monomer solution is added slowly to a rapidly stirred solution of 30 grams of sorbitan monooleate (SMO) in 320 g of Shellflex 131. The resulting W/O emulsion is sparged with nitrogen, warmed to 50° C. and treated with a solution of 0.10 g of bis azoisobutyronitrile (Dupont VAZO) in 2 milliters of benzene. Samples are taken every 30 minutes. The first one actually immediately before the addition of the initiator. To a solution of 0.25 ml of Tergitol NP-33 in 95 ml of water is added 5 ml of the sample emulsion. The mixture is stirred rapidly for 30 minutes and then treated with 2 g of sodium chloride to reduce the viscosity of the solution. The reaction is monitored by GLC. It is found that at the port temperature used, retroquaternization is complete, so that upon completion of the copolymerization reaction, before equilibration, the acrylamide percentage found can be used to calculate the approximate quat content of the copolymer.

The gas-liquid chromatograph is equipped with a 6 foot by 0.25 inch all glass column. The liquid phase is 15% OV-3 and 0.1% Poly A-135. The polymer solutions are injected at a port temperature of 200° C. The details are listed in the following table:

TABLE III

| Sample | Time Hours | Acrylamide Wt % | Moles | DMAEMA Wt % | Moles |
|---|---|---|---|---|---|
| 1 | 0 | 0.279 | 1.000 | 0.985 | 1.000 |
| 2 | 1 | 0.218 | 0.779 | 0.760 | 0.771 |
| 3 | 1.5 | 0.209 | 0.746 | 0.659 | 0.670 |
| 4 | 2.5 | 0.162 | 0.578 | 0.410 | 0.417 |
| 5 | 3 | 0.138 | 0.484 | 0.304 | 0.308 |
| 6 | 4 | 0.121 | 0.433 | 0.163 | 0.165 |
| 7 | 6 | 0.107 | 0.395 | 0.058 | 0.072 |
| 8 | 6.5 | 0.099 | 0.355 | 0.046 | 0.057 |
| 9 | 7 | 0.100 | 0.357 | 0.028 | 0.035 |

As can be seen from the Table, after 7 hours g.l.c. shows only 3.5% residual DMAEMA but 35.7% acrylamide, indicating an approximate quat content of 35% (based on the DMAEMA in the copolymer). The percentage quaternization as determined by g.l.c. is generally in good agreement with the values obtained on similar systems by Nmr analysis.

EXAMPLE 9B

Acrylamide/DMAEMA 3/1 Molar pH 7.0

To a solution of 41.9 grams of glacial acetic acid in 350 grams of tap water is added 109.6 grams of dimethylaminoethyl methacrylate (DMAEMA), followed by 148.7 grams of acrylamide (AM). The monomer solution pH is 7.0. It is added slowly to a rapidly stirred solution of 30 grams of sorbitan monooleate (SMO) is 320 grams of Shellflex 131. The resulting emulsion is sparged with nitrogen, warmed to 50° C. and treated with a solution 0.10 grams of bis azoisobutyronitrile (DuPont VAZO) in 2 milliliters of benzene. The polymerization began after a 30 minute induction period. Samples are withdrawn every hour and the residual monomer content determined by gas-liquid chromatography. After 5 hours the DMAEMA had completely disappeared and 20% of the acrylamide was recovered by GLC. This indicates that ≈60% of the DMAEMA has been quaternized by the acrylamide. A small portion of the monomer solution was stored at 25° C. for 24 hours. The NMR spectrum showed that 50% of the DMAEMA had been quaternized.

EXAMPLE 9C

Acrylamide/DMAEMA 2/1 Molar pH 7.7

To a solution of 40 grams of acetic acid in 350 grams of water is added 131 grams of DMAEMA followed by 119 grams of acrylamide. The pH is 7.7. The rest of the procedure is the same or that followed in Example A. After 5 hours g.l.c. analysis showed no DMAEMA present while 49.5% of the acrylamide was recovered which indicates that ≈99% of the DMAEMA had been quaternized. A small sample of the monomer solution was stored for 24 hours at 25° C. The NMR spectrum showed that 73% of the DMAEMA had been quaternized.

EXAMPLE 9D

Acrylamide/DMAEMA 2/1 Molar pH 6.0

The procedure of Example B is repeated except that the pH of the monomer solution is adjusted to 6.0 with 12 grams of glacial acetic acid. After five hours G.L.C. analysis showed there was no DMAEMA monomer remaining and only 8% of the acrylamide was recovered indicating that only ≈16% of the DMAEMA had been quaternized.

EXAMPLE 9E

Acrylamide/DMAEMA 2/1 Molar pH 7.0

To a solution of 50.0 grams of acetic acid in 350 grams of water is added 131 grams of DMAEMA followed by 119 grams of acrylamide. The pH of the solution is 7.0 without any adjustment. The rest of the procedure is the same as followed in Example A. After 5 hours G.L.C. analysis showed there was no DMAEMA monomer remaining, while 33% of the acrylamide was recovered. This indicates that ≈66% of the DMAEMA had been quaternized.

EXAMPLE 9F

Acrylamide/DMAEMA 2/1 Molar pH 7.7

This example demonstrates the effect of reaction temperature on the quat content. Example 9C was repeated except that the temperature was raised to 85° C. before the initiator was added. After 6 hours G.L.C. analysis showed no DMAEMA and no acrylamide present. This indicates that none of the DMAEMA had been quaternized.

The products prepared (or reacted) in the above examples can be represented by the following formulae.

1. DMAE-AM quanterary ammonium chloride is

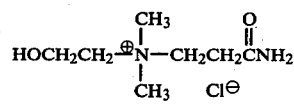

Examples 1, 4, 5

2. DMAE-AN quaternary ammonium chloride is

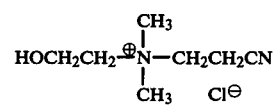

Example 2

3. DMAEMA-AM quaternary ammonium chloride is

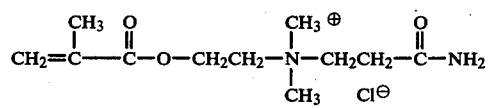

Example 3

4. Polymer of DMAEMA-AM quaternary ammonium chloride is

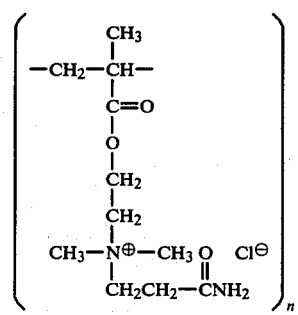

Examples 6, 7

Polymer of DMAEMA with AM is

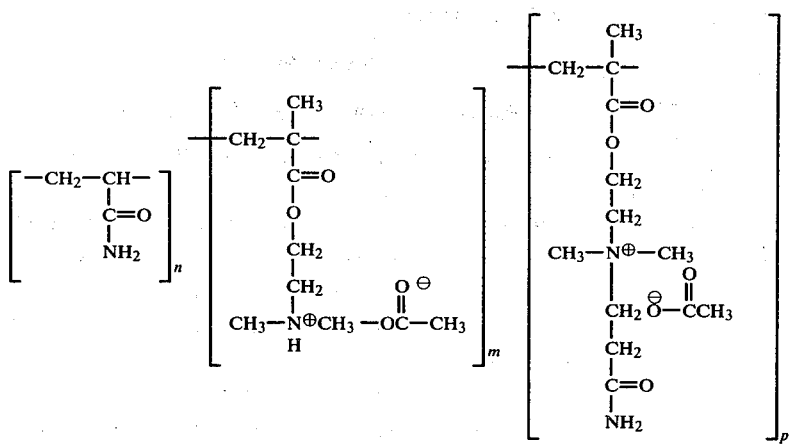

Examples 8, 9, 9A, 9B, 9C, 9D, 9E, 9F

The above examples are presented by way of illustration and not of limitation. Other modifications will be evident to those skilled in the art. For example, substituted acrylamides can also be employed for example, those of the formula

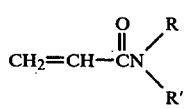

where R is hydrogen or a substituted group, for example alkyl, and R' is a substituted group, for example alkyl.

Other commercially available polymerizable tertiary amines can also be employed for example:

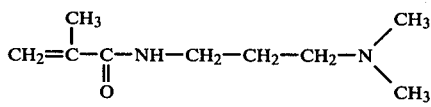

instead of DMAEMA.

In addition, the polymerizable compositions of this invention can be copolymerized with other polymerizable monomers such as those monomers containing polymerizable unsaturated groups.

USES

These compounds are useful in the clarification of water containing oil or suspended solids and especially oil coated solids. The applications include the resolution of oil field emulsions, oil in water emulsions resulting from petroleum refinery processes, and emulsions of cutting and rolling oils from metal working industries. The solids include silt, colloidal sulfur, organic polymers such as rubber and plastics, sewage sludge, and iron oxide from blast furnaces and steel manufacturing operations.

The compounds may be used alone or in combination with other materials including anionic polymers and inorganic coagulants such as alum, ferric chloride, zinc chloride, etc. They often allow a substantial reduction in the amount of the inorganic coagulants required for water clarification, and sometimes even their complete elimination. The reduction or elimination of the need for inorganic coagulants usually results in a reduction in the volume of sludge and a consequent lowering of disposal costs.

These compounds may be used in simple settling tanks, or in centrifuges. They are particularly effective in air flotation cells.

FIELD EXAMPLES

The compositions of this invention are very effective in the resolution of oil-in-water emulsions, as illustrated by the following examples.

Use Example A

At an oil field, compound 9B converted O/W petroleum emulsions to clear water at concentrations of 5-10 ppm (without the use of zinc chloride, which previously was required for good resolution).

Use Example B

At a refinery, the water effluent turbidity was reduced to 10-14 ppm of oil by the use of 0.06 to 0.10 ppm of compound 9C, together with 10 ppm of alum and 1 ppm of polyethylene polyamines. The alum requirement was reduced from 19 ppm to 10 ppm.

The compositions of this invention are very effective in the clarification of water containing suspended solids, as illustrated by the following examples.

Use Example C

At an oil refinery, raw river water was clarified for process use by treatment with 3 ppm Compound 9A, together with 25 ppm of alum. The turbidity was reduced to 10 ppm.

Use Example D

At a steel plant, a waste stream containing mostly iron oxide was treated with 1 ppm of compound 9C and 0.25 ppm of a high molecular weight anionic polymer. The turbidity was reduced to 1.5 FTU (formazine turbidity units) without the addition of ferric chloride or other inorganic coagulants.

Use Example E

At a polymer plant, effluent water from an A.P.I. separator, contaminated with organic solids was clarified by treatment with 0.375 ppm of Compound 9B.

The compositions of this invention are very effective in removing oil and oil coated solids from effluent waters when used in an air flotation cell such as a Wemco Depurator, as illustrated by the following examples.

Use Example F

At an oil field, the raw water contained 140 ppm oil. Without chemical treatment, the Wemco Depurator reduced the oil lever to 125 ppm. When 1.5 ppm of Compound 9C was added to the Wemco Depurator, the oil content was reduced to below 19 ppm.

Use Example G

At a petroleum refinery, the effluent water from an A.P.I. separator contained 150 ppm oil and solids and was unchanged by the Wemco Depurator alone. Addition of 5 ppm of Compound 9C reduced the impurities to 20 ppm.

Use Example H

At a petroleum refinery the oily effluent water was improved from 70 ppm to 20 ppm by treatment with 3 ppm of Compound 9C in a "Quadricell" air flotation cell.

Use Example I

At a petroleum refinery, treatment with Compound 9C in a Wemco Depurator removed both oil and colloidal sulfur from the effluent water.

It is understood that the above examples are for illustration purposes only and modifications can be made without departing from the concept of the present invention.

We claim:

1. A composition of the formula $$R-\overset{R'}{\underset{R'}{N^{\oplus}}}-CH_2CH_2CN \quad X^{\ominus}$$

where R is a methacrylamidoalkyl group or acrylamidoalkyl group, each R' is an alkyl group and $X^{\ominus}$ is an anion.

2. The composition of claim 1 where R is $$CH_3=\overset{H}{\underset{}{C}}-\overset{O}{\underset{}{\overset{\|}{C}}}-\overset{H}{\underset{}{N}}-CH_2-CH_2- \quad \text{or}$$

$$CH_3-\overset{CH_3}{\underset{}{C}}\mathrm{-\!-\!-}\overset{O}{\underset{}{\overset{\|}{C}}}-\overset{H}{\underset{}{N}}-CH_2-CH_2-.$$

3. The composition of claim 1 where $X^{\ominus}$ is a chloride or carboxylate ion.

4. The composition of claim 2 where $X^{\ominus}$ is a chloride or carboxylate ion.

5. A process of preparing the composition of claim 1 which comprises reacting conjugate acid salts of a compound of the formula $$\overset{R'}{\underset{R'}{\overset{|}{RN,}}}$$

where R is a polymerizable group terminated in $$\overset{H}{\underset{}{\overset{|}{CH_2=C-}}} \quad \text{or} \quad \overset{CH_3}{\underset{}{\overset{|}{CH_2=C}}}$$

moieties, and each R' is an alkyl group, with a compound of the formula $CH_2=CH-CN$, and where the N of $$\overset{R'}{\underset{R'}{\overset{|}{RN}}}$$

is attached to three carbon atoms.

* * * * *

UNITED STATES PATENT AND TRADEMARK OFFICE
CERTIFICATE OF CORRECTION

PATENT NO. : 4,310,472
DATED : January 12, 1982
INVENTOR(S) : Rudolf S. Buriks, Allen R. Fauke, David W. Griffiths It is certified that error appears in the above—identified patent and that said Letters Patent is hereby corrected as shown below:

Col. 2, lines 56-61, change the equation to read:

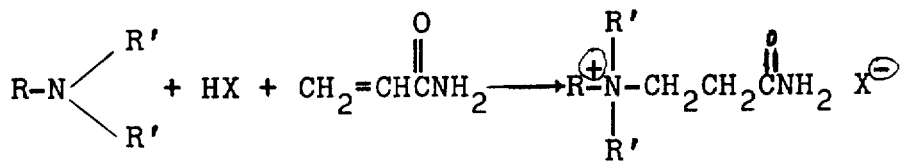

Col. 2, line 62, change "HA" to

--- HX ---.

and "A" to

--- X$^{\ominus}$ ---.

Col. 2, line 63, change "R, R', and R" " to

--- R and R' ---.

Col. 4, line 62, change "the R's" to

--- the R' 's ---.

UNITED STATES PATENT AND TRADEMARK OFFICE
CERTIFICATE OF CORRECTION

PATENT NO. : 4,310,472
DATED : January 12, 1982
INVENTOR(S) : Rudolf S. Buriks, Allen R. Fauke, David W. Griffiths It is certified that error appears in the above—identified patent and that said Letters Patent is hereby corrected as shown below:

Col. 5, line 32, change "1:1:2" to

--- 1:2:2 ---.

Col. 11, lines 27-32, change the "R" in the formula to

--- R' ---.

Col. 11, line 33, change "R" to

--- one R' ---.

UNITED STATES PATENT AND TRADEMARK OFFICE
CERTIFICATE OF CORRECTION

PATENT NO. : 4,310,472
DATED : January 12, 1982
INVENTOR(S) : Rudolf S. Buriks, Allen R. Fauke, David W. Griffiths It is certified that error appears in the above—identified patent and that said Letters Patent is hereby corrected as shown below:

Col. 11, line 34, before "R'", insert --- the other ---.

Signed and Sealed this

Thirtieth Day of August 1983

[SEAL]

Attest:

Attesting Officer

GERALD J. MOSSINGHOFF
Commissioner of Patents and Trademarks